United States Patent [19]

DiNello

[11] Patent Number: 4,663,278
[45] Date of Patent: May 5, 1987

[54] AGGLUTINATION DEPENDENT ENZYME CHANNELING IMMUNOASSAY

[75] Inventor: Robert K. DiNello, Cupertino, Calif.

[73] Assignee: Syva Company, Palo Alto, Calif.

[21] Appl. No.: 582,146

[22] Filed: Feb. 24, 1984

Related U.S. Application Data

[63] Continuation of Ser. No. 373,760, Apr. 30, 1982, abandoned.

[51] Int. Cl.$^4$ .................. G01N 33/546; G01N 33/535
[52] U.S. Cl. ........................................ 435/7; 435/810; 436/523; 436/533; 436/534; 436/808
[58] Field of Search .................. 435/4, 7, 180, 181, 435/810; 436/532, 533, 534, 536, 537, 808, 523

[56] References Cited

U.S. PATENT DOCUMENTS

| | | | |
|---|---|---|---|
| 4,108,972 | 8/1978 | Dreyer | 436/533 |
| 4,184,849 | 1/1980 | Combiano et al. | 435/7 |
| 4,189,466 | 2/1980 | Ainis et al. | 435/7 |
| 4,193,983 | 3/1980 | Ullman et al. | 435/7 |
| 4,233,402 | 11/1980 | Maggio et al. | 435/7 |
| 4,275,149 | 6/1981 | Litman et al. | 435/7 |
| 4,299,916 | 11/1981 | Litman et al. | 435/7 |
| 4,486,530 | 12/1984 | David et al. | 435/7 |

Primary Examiner—Esther M. Kepplinger
Attorney, Agent, or Firm—Bertram I. Rowland; Theodore J. Leitereg; Carole F. Barrett

[57] ABSTRACT

A novel agglutination assay is provided which brings together through the intermediacy of the binding of specific binding pair members particles which differ by having different members of a signal producing system. The signal producing system is characterized by having two enzymes which are related by having the product of one enzyme being the substrate of the other, where the reaction of the second enzyme results in a product providing a detectable signal, desirably including a scavenger for the product of the first enzyme. The amount of product providing the detectable signal which is produced is related to the amount of analyte in the media. The composition and ratio of particles can be provided in reagent kits to optimize the assay results.

10 Claims, No Drawings

AGGLUTINATION DEPENDENT ENZYME CHANNELING IMMUNOASSAY

This is a continuation of copending application U.S. Ser. No. 373,760, filed Apr. 30, 1982, now abandoned.

BACKGROUND OF THE INVENTION

1. Field of the Invention

The usefulness of macromolecules to be able to distinguish a specific compound in a complex mixture by binding to a specific compound is the basis for the greatly expanding usefulness of specific binding pair assays, most frequently immunoassays employing antibodies. In the decade spanning 1970–1980, numerous new assays were disclosed in the scientific and patent literature based on a wide variety of different reagents, protocols, and labels. Different approaches were employed to reduce background interference or matrix effects on assay results, to improve labeling techniques, to minimize unmodulatable signals, and to expand the range of sensitivity.

As each new assay has been developed, efforts are made to retain as many of the advantages which have already been realized, while further adding additional advantages. Therefore, there are continued efforts to modify assays which have been demonstrated to have a wide variety of desirable characteristics to enhance one or more characteristics, while substantially retaining the other desirable characteristics.

One group of assays known as "homogeneous" immunoassays relies on the fact that the assays do not require a separation step. Therefore, the assays must be relatively resistant to matrix effects resulting from the physiological fluids, such as blood and urine, which are frequently analyzed. As increasing sensitivity is desired to be able to analyze lower concentrations of a variety of analytes, the matrix or background effects can become extremely troublesome. Therefore, in developing assays of greater sensitivity, it is necessary that they be relatively unaffected by variations in sample composition.

2. Description of the Prior Art

U.S. Pat. No. 4,275,149 described the use of particles in a "homogeneous" immunoassay. Also, a substantial number of references are set forth in the patent. U.S. Pat. Nos. 4,138,213; 4,141,965 and 4,164,558 are illustrative of conventional agglutination techniques for use in immunoassays.

SUMMARY OF THE INVENTION

Novel agglutination assays are provided employing specific binding pairs for causing agglutination of particles. The detection system for agglutination employs a two-enzyme system where the enzymes are related by the product of one being the substrate of the other, where the second enzyme provides a product affording a detectable signal.

DESCRIPTION OF THE SPECIFIC EMBODIMENTS

Method and compositions are provided for detecting an analyte which is a member of a specific binding pair. The method is employed for determining organic compounds at low concentrations in a wide variety of media, particularly physiological media, where the compounds are of physiological interest. The analyte may be naturally occurring or synthetic, may be naturally present or administered.

The method employed has as an assay medium, a continuous liquid aqueous phase and a homogeneously dispersed solid phase comprised of discrete small particles having relatively slow settling rates. All of the particles include a member of the specific binding pair which serves to agglutinate the particles. The particles are divided into two groups, one group having a first enzyme and the other group having a second enzyme, where the enzymes are related by one of the enzymes having a product which serves as the substrate for the other enzyme. The other or second enzyme produces a product, directly or indirectly, which provides a detectable signal.

Depending upon the specific binding pair members and the analyte, various protocols may be employed for bringing together the particles and the sample containing the analyte. The amount of agglutination or clumping together of the particles will be related to the amount of analyte in the medium. Depending upon the amount of agglutination, the average distance between the two enzymes will vary, which will vary the production of the product providing the detectable signal. The amount of the product providing the detectable signal which is produced can, therefore, be related to the amount of analyte in the medium. By preparing samples having a known amount of analyte and performing the assay with the samples, a standard curve can be prepared which will relate the observed signal to the amount of analyte in the assay medium.

In performing the subject method, there will be the two particles, which may be the same or different, at least distinguished by the different enzymes, the necessary substrates, and ancillary reagents. By appropriate choice of the reagents, one can perform assays under a wide variety of conditions and tailor the assays in accordance with the particular analyte and its complementary specific binding pair member.

DEFINITIONS

Analyte—the compound or composition to be measured, which may be a ligand, which is mono- or polyepitopic, antigenic or haptenic, a single or plurality of compounds which share at least one common epitopic site or a receptor.

Specific binding pair ("mip")—two different molecules, where one of the molecules has an area on the surface or in a cavity which specifically binds to a particular spatial and polar organization of the other molecule. The members of the specific binding pair are referred to as ligand and receptor (antiligand). For the most part, the molecules will be members of an immunological pair. For convenience, all specific bond pair members will be referred to as a mip.

Ligand—any organic compound for which a receptor naturally exists or can be prepared.

Receptor ("antiligand")—any compound or composition capable of recognizing a particular spatial and polar organization of a molecule i.e. epitopic site. Illustrative receptors include naturally occuring receptors, e.g. thyroxine binding globulin, antibodies, enzymes, Fab fragments, Fv fragments, lectins and the like.

Ligand Analog—a modified ligand which can compete with the analogous ligand for a receptor, the modification providing means to join a ligand analog to another molecule. The ligand analog will normally differ from the ligand by more than replacement of a hydrogen with a bond which links the ligand analog to a hub or label.

Poly(ligand-analog)—a plurality of ligands or ligand analogs joined together covalently, normally to a hub nucleus. The hub nucleus is a polyfunctional material, normally polymeric, usually having a plurality of functional groups e.g. hydroxy, amino, mercapto, ethylenic, etc. as sites for linking. The hub nucleus may be water soluble or insoluble, preferably water soluble, and will normally be at least about 35,000 molecular weight and may be 10 million or more molecular weight, but usually under 600,000, more usually under 300,000. Illustrative hub nuclei include polysaccharides, polypeptides, including proteins, nucleic acids, ion exchange resins and the like. Water insoluble hub nuclei can be the same as those indicated for the particle.

Particle (solid phase)—the particle is a discrete solid particle, which may be swelled or remain unswelled by the liquid phase, and composed of a wide variety of both hydrophobic and hydrophilic materials. The particles will be solid, hollow or porous, having a substantially smooth or irregular surface, having a primarily concave or convex surface, preferably being porous and having channels or indentations, which can be widely varied as to the size of molecule or assembly which is excluded. The particles will be readily dispersible in an aqueous medium, and either polyfunctionalized or capable of polyfunctionalization for linking of other molecules. Usually, the particles will be substantially transparent to light in a substantial wavelength range between 300 and 800 nm, preferably through the range or be opaque over the entire ultraviolet and visible range.

Label—the label may be any molecule conjugated to another molecule. The definition as to which molecule is the label is arbitrarily chosen. In the subject invention, the labels will be the specific binding pair molecule that is conjugated to the particle, or a molecule which is part of the signal producing system that is conjugated to a member of the specific binding pair or to a particle.

Signal producing system—the signal producing system is comprised of at least two enzymes, a first and second enzyme, where the first enzyme produces a product which serves as the substrate of the second enzyme. The second enzyme transforms the substrate by itself or in combination with other substrates to produce, directly or indirectly, a product which results in a change in a detectable signal. The signal producing system therefore includes the enzymes, appropriate substrates, and any other materials which are involved in the change in the detectable signal.

Enzyme particle conjugate—a particle conjugate having an enzyme label, which enzyme is a member of the signal producing system.

METHOD

The subject assay is carried out in an aqueous zone at a moderate pH, generally close to optimum assay sensitivity, without separation of the assay components or products. The assay zone for the determination of analyte is prepared by employing an appropriate aqueous medium, normally buffered, the unknown sample, which may have been subject to prior treatment, the particle conjugate, the binding pair member conjugate, all of the materials required for the signal producing system for producing a detectible signal, as well as members of the specific binding pair or their analogs, as required.

The presence of ligand or its homologous receptor (antiligand) in the unknown will affect the partition of the members of the signal producing system between individual particles containing only one member of the system and masses of agglutinated particles containing both members.

In carrying out the assay, an aqueous medium will normally be employed. Other polar solvents may also be included, usually oxygenated organic solvents of from 1–6, more usually from 1–4 carbon atoms, including alcohols, ethers and the like. Usually these cosolvents will be present in less than about 40 weight percent, more usually in less than about 20 weight percent.

The pH for the medium will usually be in the range of about 4–11, more usually in the range of about 5–10, and preferably in the range of about 6.5–9.5. The pH is chosen so as to maintain a significant level of specific binding by the receptor while optimizing signal producing efficiency. In some instances, a compromise will be made between these two considerations. Various buffers may be used to achieve the desired pH and maintain the pH during the determination. Illustrative buffers include borate, phosphate, carbonate, Tris, barbital and the like. The particular buffer employed is not critical to this invention but in individual assays, one buffer may be preferred over another.

Moderate temperatures are normally employed for carrying out the assay and usually a constant temperature during the period of the measurement, particularly for rate determinations. The temperature for the determination will generally be in the range of from about 10°–50° C., more usually from about 15°–40° C.

The concentration of analyte which may be assayed will generally vary from about $10^{-4}$ to $10^{-20}$, more usually from about $10^{-6}$ to $10^{-16}$M. Considerations such as whether the assay is qualitative, semi-quantitative or quantitative, the particular detection technique and the concentration of the analyte of interest will normally determine the concentration of the other reagents.

While the concentrations of the various reagents in the assay medium will generally be determined by the concentration range of interest of the analyte, the final concentration of each of the reagents will normally be determined empirically to optimize the sensitivity of the assay over the range of interest. The total binding sites of the members of the specific binding pair which are reciprocal to the analyte will be not less than about 0.1 times the minimum concentration of interest based on binding sites of analyte and usually not more than about 1,000 times the maximum concentration of interest based on analyte binding sites, usually about 0.1 to 100 times, more usually about 0.3–10 times the maximum concentration of interest. By concentration is intended the available concentration, that is, the concentration at saturation, and not necessarily the actual concentration where members of the specific binding pair may not be equally available for binding.

Depending upon the particular signal producing system, as well as the manner in which the specific binding pair members are employed, the amount of the various conjugates can be varied quite widely. For example, one could have very large excesses of the mip label in the particle conjugate, where the analyte is polyepitopic and serves as a bridge. By contrast, where different mips are used in the particle conjugates and the complementary mip particle conjugate is initially combined with the analyte containing sample, the number of mips in the complementary particle conjugate would be related to the concentration range of interest of the analyte. By employing various concentrations of the various reagents with analyte at concentrations in the range of interest, one would obtain ratios which would optimize the assay response.

The order of addition of the various reagents may vary widely, depending upon the particular labels, the nature of the conjugates, the nature of the analyte, and the relative concentrations of the analyte and reagents. Also affecting the order of addition is whether an equilibrium mode or rate mode is employed in the determination.

Since with many receptors, the association of the mips is almost irreversible during the time period of the assay, one will normally avoid combining the particle conjugates, prior to the addition of the analyte, where the two conjugates are reciprocal or homologous mips. By contrast, where the two conjugates have the same mip, one could combine them prior to introduction of the unknown sample into the assay medium. Regardless of the nature of the analyte, all the reagents can be added simultaneously and either a rate or equilibrium determination made.

One or more incubation steps may be involved in preparing the assay medium. For example, it may be desirable to incubate an antigen analyte with one particle conjugate. In addition, it may be desirable to have a second incubation after addition of the second particle conjugate. Whether to employ an incubation period and the length of the incubation period, will depend to a substantial degree on the mode of determination--rate or equilibrium--and the rate of binding of the receptor to the ligand. Usually, incubation steps will vary from about 0.5 min to 6 hrs, more usually from about 5 min, to 1 hr. Incubation temperatures will generally range from about 4° to 50° C., more usually from about 15° to 37° C.

While the ratios of the mip containing reagents to the analyte will be related to the amount of analyte and the protocol, other reagents will normally be present in excess. Particularly, the amount of substrate(s) present should not be rate limiting at the highest production of product. Other reagents, such as buffers and stabilizing reagents, will be present in sufficient amounts, so that matrix effects will be minimized.

After the reagents are combined, the signal will then be determined. The method of determination is normally the observation of electromagnetic radiation, particularly ultraviolet and visible light, either absorption or emission. Desirably, the signal will be read as electromagnetic radiation in the ultraviolet or visible region, particularly from about 250 to 750 nm, usually from about 350 to 650 nm.

The temperature at which the signal is observed will generally range from about 10° to 50° C., more usually from about 15° to 40° C.

Standard assay media can be prepared which have known amounts of the analyte. The observed signal for the standard assay media may then be plotted, so as to relate concentration to signal. Once a standard curve has been established, a signal may be directly related to the concentration of the analyte.

The time for measuring the signal will vary depending on whether a rate or equilibrium mode is used, the sensitivity required, the nature of the signal producing system and the like. For a rate mode the times between readings will generally vary from about 5 sec. to 6 hrs, usually about 10 sec. to 1 hr. For the equilibrium mode, after a steady state is achieved, a single reading may be sufficient or two readings over any covenient time interval may suffice.

The analyte (ligand) may be mono- or polyepitopic. In most situations this difference need not affect the manner in which the assay is performed. Where the analyte is a ligand, the mips in the particle conjugates may be either ligand or receptor, being the same or different, normally at least one being a receptor. However, where the mips of both particle conjugates are receptors, the ligand must be polyepitopic or be provided in polyepitopic form, employing a poly(ligand analog) as an additional reagent. That is, a sandwich technique is employed where the poly(ligand analog) binds to the particle conjugates and provides epitopic sites for agglutinating the particle conjugates.

Where receptor is the analyte, the particle conjugates may have the same or different members of the specific binding pair, with the proviso that receptor is polyvalent when ligand is involved in both conjugates.

In the event that the analyte and the two particulate conjugates all have or contain the same member of the specific binding pair, then the homologous member must be added and it must be provided in polyepitopic form, either as an antibody, or a polyvalent receptor, where it is a receptor or as polyhapten (poly(ligand analog)), where it is a ligand.

MATERIALS

The components employed in the assay will be the particle conjugates, the other reagents which are the remaining members of the signal producing system, and the analyte, and as appropriate, poly(ligand analog) and polyvalent receptor. Employed in the preparation of the reagents will be the particles or beads and members of the signal producing system.

Analyte

The ligand analytes of this invention are characterized by being monoepitopic or polyepitopic. The polyepitopic ligand analytes will normally be poly(amino acids) i.e. polypeptides and proteins, polysaccharides, nucleic acids and combinations thereof. Such combinations and assemblages include bacteria, viruses, chromosomes, genes, mitochondria, nucleii, cell membranes and the like.

For the most part, the polyepitopic ligand analytes employed in the subject invention will have a molecular weight of at least about 5,000 and usually at least about 10,000. In the poly(amino acids) category, the poly(amino acids) of interest will generally be from about 5,000 to 5 million molecular weight, more usually from about 20,000 to about 1 million molecular weight; among the hormones of interest, the molecular weights will usually range from about 2,000 to 60,000.

A number of polyepitopic ligands are described in U.S. Pat. No. 4,275,149, bridging columns 12-17, which disclosure is incorporated herein by reference.

The monoepitopic ligand analytes will generally be from about 100 to 2,000 molecular weight, more usually from about 125 to 1,000 molecular weight.

Monoepitopic analytes are described in U.S. Pat. No. 4,275,149, bridging columns 17 and 18, which disclosure is incorporated herein by reference. Also included in the aforementioned patent is a description of the ligand analog, bridging columns 18 and 19, which disclosure is also incorporated herein by reference.

Signal Producing System

The signal producing system involves the two enzymes and the associated reagents. As already indicated, the two enzymes are related in that the product of one is the substrate of the other and the second enzyme produces a product, either directly or indirectly, which results in a change in a detectable signal. Desirably, an additional reagent will be provided, which acts as a scavenger of the product of the first enzyme, to minimize any reaction occurring away from the agglutinated particles. The product which provides the detectable signal will normally be a dye or fluorescer, so that the signal may be measured by a change in light absorption or emission.

In chosing a signal producing system, there will be a number of considerations. Essential to the system is that there are two enzymes, where the product of one is the substrate of the other. Furthermore, the second enzyme must provide, either directly or indirectly, a compound which allows for a change in a detectable signal. Thirdly, each of the enzymes should have relatively high turn-over numbers, desirably the second enzyme having a higher turn-over number than the first. Also, considerations which will affect the choice of enzymes are their stability, presence in samples to be assayed, sensitivity to chemical modification and non-specific effects, pH and ionic strength rate profiles, and the like.

A large number of enzymes are set forth in accordance with the classification of the International Union of Biochemistry in U.S. Pat. No. 4,275,149, which listing is incorporated herein by reference.

Of particular interest are the enzymes which are in Class I. Oxidoreductases and Class III, hydrolases, although enzymes of Class II, transferases, Class IV, lyases and Class V, isomerases, may also be of interest in particular situations.

Various combinations of enzymes may be employed. In one set of combinations, the ability to measure NAD and NADP or their reduced products is employed. In these combinations, oxidoreductases dependent on NAD are employed with an enzyme which provides a substrate for the oxidoreductases. A wide variety of enzyme types and reactions may be employed to produce the substrate, many of the enzymes being part of carbohydrate metabolism. A substantial number of these enzymes will be involved in the formation and transformation of phosphate esters. Among other reactions which may be involved are carbon-carbon bond cleavage by lyases, isomerization involving keto-aldehyde transformations, and decarboxylation.

While the above exemplary combinations have been limited to two enzymes, obviously, systems could be devised which would have three or more enzymes. For example, one could have two enzymes on one particle, each enzyme producing a different obligatory substrate for a third enzyme, which would then combine the two substrates to produce a product providing a detectable signal. However, in most situations, the system becomes extremely complicated in having such a wide variety of materials present, so that any advantages in reduction in background will be offset by the complications introduced by the additional enzyme. Therefore, for the most part, the system will only involve two enzymes.

The effect of agglutination, should involve at least a two, preferably a 10-fold increase, more preferably a 100-fold rate increase in the change in signal as compared to the rate of reaction in the absence of agglutination.

Desirably, to further enhance the differential in rate between the agglutinated particles and individual particles in the bulk medium, a scavenger can be employed which transforms the product of the first enzyme into a less reactive, preferably an inactive, substrate for the second enzyme. For example, where hydrogen peroxide is the product of the first enzyme, catalase may be employed to destroy the hydrogen peroxide. Where a group is being removed or added to a particular substrate, the scavenger could either reverse the reaction, recreate the substrate for the first enzyme or modify the product by reduction, oxidation, acylation, glycosylation, or the like.

Of particlar interest are combinations involving sugars, where in a first step a transferase, hydrolase, lyase or isomerase, particularly involving a phosphate ester, produces a substrate of a NAD(P) dependent oxidoreductase. Particularly useful are mono-phosphate monosaccharides of from 3 to 6 carbon atoms as enzyme substrates in the oxidoreductase reaction.

The following table indicates a number of illustrative examples where precursors for oxidoreductases are formed and the course of the reaction of the NAD dependent enzymes is followed by the transformation of the NAD or NADP to or from its reduced form. In each example both enzymes are signal labels.

TABLE I

| | Category I.U.B. | Enzyme | Exemplary Reaction |
|---|---|---|---|
| 1. | 2.7.1 | Hexokinase | glucose + ATP→glucose-6-phosphate + ADP |
| | 1.1.1 | glucose-6-phosphate dehydrogenase | glucose-6-phosphate + NADP→6-P—glucuronate NADPH |
| 2. | 4.1.2 | aldolase | fructose-1,6-diP→dihdroxyacetone-P + glyceraldehyde-3-P |
| | 1.2.1 | glyceraldehyde-P dehydrogenase | glyceraldehyde-3-P + NAD→3-phosphoglycerate + NADH |
| 3. | 3.1.3 | alkaline phosphatase | dihydroxyacetone diphosphate→dihydroxyacetone phosphate |
| | 1.2.1 | glycerol -3-P dehydrogenase | dihydroxyacetone phosphate + NADH→glyceryl phosphate + NAD |
| 4. | 2.7.1 | pyruvate kinase | phosphoenol pyruvate + ADP→pyruvate + ATP |
| | 1.1.1 | lactate dehydrogenase | pyruvate + NADH→ + NAD |
| 5. | 3.1.3 | alkaline phosphatase | 1,6-glucosyl diphosphate→G-6-P |
| | 1.1.1 | glucose-6-phosphate dehydrogenase | G-6-P + NADP→6-P—glucuronate + NADPH |
| 6. | 5.4.2 | triose phosphate isomerase | glyceraldehyde-3-P→dihydroxyacetone phosphate |
| | 1.2.1 | α-glycerol-3-P dehydrogenase | dihydroxyacetone phosphate + NADH→glyceryl phosphate + NAD |
| 7. | 3.1.3 | alkaline phosphatase | D-sorbitol phosphate→D-sorbital |
| | 1.1.1 | α-D-hexitol dehydrogenase | D-sorbital + NADP→α-D-glucopyranose + NADPH |

TABLE I-continued

| | Category I.U.B. | Enzyme | Exemplary Reaction |
|---|---|---|---|
| 8. | 5.4.2 | phosphoglucomutase | α-glucose-1-phosphate→glucose-6-phosphate |
| | 1.1.1 | glucose-6-phosphate dehydrogenase | glucose-6-phosphate + NAD→ + NADH |
| 9. | 4.1.1 | pyruvate decarboxylase | pyruvate→acetaldehyde |
| | 1.1.1 | alcohol dehydrogenase | acetaldehyde + NADH→ethanol + NAD |
| 10. | 4.2.1 | fumarase | fumarate→malate |
| | 1.1.1 | malate dehydrogenase | malate + NAD→oxalacetate + NADH |
| 11. | 4.2.1 | aconitase | cis-aconitate→isocitrate |
| | 1.1.1 | isocitrate dehydrogenase | isocitrate + NAD→α-oxoglutarate + NADH |

Another combination of enzymes involves the formation of hydrogen peroxide, where the resulting reaction catalyzed by peroxidase of the hydrogen peroxide with a chemiluminescent material, e.g. luminol, produces light. Besides luminol, other 2,3-dihydro-1, 4-phthalazine-diones may be employed. These include the 5-amino-6,7,8-trimethoxy- and dimethylamino[ca]benz analog. Other compounds are the 2,4,5-triphenylimidazoles, with lophine, as the common name for the parent, and the para-dimethylamino and -methoxy substituted compounds also finding use. The chemiluminescent compound may be the direct source of light or may be allowed to interact with an acceptor, such as 9,10-dibromoanthracene, which will then emit light. Alternatively one can provide a wide variety of dye precursors which will undergo enzymatically catalyzed reactions with hydrogen peroxide to produce the colored form which can be detected.

The following table indicates a number of these reactions.

TABLE II

| | Enzyme Category | Enzyme | Exemplary Reaction |
|---|---|---|---|
| 1. | 1.1.2 | glucose oxidase | glucose + $O_2$→glucuronate + $H_2O_2$ |
| | 1.11.1 | peroxidase | $H_2O_2$ + luminol→products + hv |
| 2. | 1.7.3 | uricase | urate + $O_2$→allantoin + $H_2O_2$ |
| | 1.11.1 | peroxidase | $H_2O_2$ + O—dianisidine→dye |
| 3. | 1.4.3 | D-amino acid oxidase | D-alanine + $O_2$→pyruvate + $H_2O_2$ |
| | 1.11.1 | catalase | $H_2O_2$ + Fe(CN)$_6^{-4}$→Fe(CN)$_6^{-3}$ |
| 4. | 1.2.3 | xanthine oxidase | xanthine + $O_2$→uric acid + $H_2O_2$ |
| | 1.11.1 | cytochrome C oxidase | $H_2O_2$ + pyrogallol→hydroxyquinone |

The next series of reactions are those which are based on two reactions involving water, normally the two reactions involving hydrolases, although synthetases may also be employed.

TABLE III

| | Enzyme Category | Enzyme | Examplary Reaction |
|---|---|---|---|
| 1. | 3.1.3 | alkaline phosphatase | 1-umbelliferyl-β-galactoside-6-P→1-umbelliferyl-β-galactoside |
| | 3.2.1 | β-galactosidase | 1-umbelliferyl-β-galactoside→1-alizarinyl-β-glucoside |
| | 3.2.1 | β-glucosidase | 1-alizarinyl-β-glucoside→alizarin + glucose |
| 3. | 3.2.1 | glucoamylase | 1-(p-nitrophenyl) 4-O—α-D-glucopyranosyl β-D-glucose→1-(p-nitrophenyl) β-D-glucoside→p-nitrophenoxide + glucose |
| 4. | 3.1.1 | cholinesterase | phenolphthalein β-glucuronide choline chloride ester→ phenolphthalein β-glucuronide |
| | 3.2.1 | β-glucuronidase | phenolphthalein β-glucuronide→β-glucuronide + phenolphthalein |
| 5. | 3.4.1 | proline iminopeptidase | L-prolyl-L-leucine p-nitroanilide→L-leucine p-nitroanilide |
| 5. | 3.4.1 | aminopeptidase | L-leucine p-nitroanilide→L-leucine + p-nitroaniline |
| 6. | 3.5.1 | urease | urea + $H_2O$→$CO_2$ + $NH_3$ |
| | 6.3.5 | NAD synthetase | ATP + deamidoNAD + $NH_3$ + $H_2O$→ADP + NAD + pyrophosphate |
| 7. | 3.1.3 | alkaline phosphatase peroxidase | 2,6-dichlorophenolindophenol-P→2,6-dichlorophenolindophenol 2,6-dichlorophenolindophenol + $H_2O_2$→dye |

The next series of combinations involves the preparation of a substrate in a first step for an enzyme which can donate or receive electrons from an acceptor or donor, with the result that there is a substantial change in the absorption spectrum of the acceptor or donor. For the most part, the second enzyme will be an oxidoreductase, particularly dehydrogenases and oxidases.

TABLE IV

| | Enzyme Category | Enzyme | Examplary Reaction |
|---|---|---|---|
| 1. | 3.1.1 | cholinesterase | butryl choline chloride→choline |
| | 1.1.99 | choline dehydrogenase | choline + phenazine methosulfate→betaine aldehyde + dye (H) |
| 2. | 2.7.1 | glycerol kinase | ATP + glycerol→L-glycerol-3-P |
| | 1.1.99 | glycerolphosphate dehydrogenase | L-glycerol-3-P + methylene blue→dihydroxyacetone phosphate + dye (H) |
| 3. | 1.1.1 | glucose dehydrogenase | β-D-gluconate + NADP→D-glucono-δ-lactone + NADPH |
| | 1.1.99 | gluconate dehydrogenase | D-gluconate + resazurin→2-keto-D-gluconate + dye (H) |
| 4. | 1.1.1 | alcohol dehydrogenase | ethanol + NAD→acetaldehyde + NADH |
| | 1.6.2 | cytochrome $b_5$ | NADH + indigo tetrasulfonate→NAD + indigotetra sulfonate (H) |

TABLE IV-continued

| | Enzyme Category | Enzyme | Examplary Reaction |
|---|---|---|---|
| 5. | 4.1.2 | deoxyriboaldolase | 2-deoxy-D-ribose-5-phosphate→D-glyceraldehyde-3-P + acetaldehyde |
| | 1.2.3 | aldehyde oxidase | acetaldehyde + 2,6-dichlorophenol-indophenol→acetic acid + dye (H) |
| 6. | 1.1.1 | alcohol dehydrogenase | ethanol + NADP→acetaldehyde + NADPH |
| | 1.6.9 | reduced NADP dehydrogenase | NADPH + trichlorophenolindophenol→ NADP + trichlorophenolindophenol (reduced) |

As previously indicated, it is desirable to have a scavenger in the solution which reduces the concentration of the product of the first enzyme in the bulk medium. The scavengers may be enzymatic or non-enzymatic and are chosen so as to minimize any non-specific interference with the assay. The particular scavenger will vary, of course, with the product of the first enzyme.

Where hydrogen peroxide is the product, various enzymatic and non-enzymatic catalysts can be employed. For an enzymatic catalyst, catalase may be employed. For a non-enzymatic catalyst, various metals and metal chelates may be employed, such as colloidal noble metals, e.g. platinum.

Scavengers may also serve as reactants to transform the product of the first enzyme to a compound which is inactive with the second enzyme. For example, an enzyme which reverses the reaction of the first enzyme, e.g. a phosphatase and a kinase, where NADH is the product of the first enzyme, one can employ a mild oxidant, such as phenozine methosulfate. Antibodies may be employed for the product. The above illustrations are only a few of the many available useful scavengers.

Particles

A wide variety of particles may be employed in this invention. The particles may be solid, porous or microarticulated or the like. Preferably, latex particles are employed, which may be modified in a variety of ways to reduce non-specific absorption.

The particles may come in a variety of sizes and colors based on the following considerations. The particles should be relatively stably dispersed during the time of the assay and preferably longer. Indefinite stability in the assay medium is not required. The particle size should be sufficiently small, so that a large number of particles will be in the solution. Also, upon agglutination, the agglomeration should not interfere with the observation of the detectable signal. For the most part, the particles will be of a diameter in the range of about 50 nm to 100$\mu$, more usually about 500 nm to 25$\mu$. For porous particles, pore size will generally vary from about 0.1 nm to under 750 nm, more usually not more than about 500 nm.

The particle size can be varied and surface area increased by breaking larger particles into smaller particles by mechanical means, such as grinding, sonication, agitation, etc.

A wide variety of materials may be employed for the particles. Many materials are commercially available or commercially available materials may be modified, so as to modify the properties of the material.

The particles can be derived from naturally occurring materials, naturally occurring materials which are synthetically modified and synthetic materials. Of particular interest are polysaccharides, particularly crosslinked polysaccharides, such as agarose, which is available as Sepharose ®, dextran, available as Sephadex ®, acrylamide, available as Biogel-p ®, cellulose, starch and the like. Other materials include polyacrylamides, polystyrene, polyvinyl alcohol, copolymers of hydroxyethyl methacrylate and methyl methacrylate, silicones, glasses, available as Bioglas ®, charcoal and the like.

The particles should be polyfunctional or be capable of being polyfunctionalized. A wide variety of functional groups are available or can be incorporated. Functional groups include carboxylic acids, aldehydes, amino groups, cyano groups, ethylenic groups, hydroxyl groups, mercapto groups, and the like. The manner of linking a wide variety of compounds to the various particles is well known and is amply illustrated in the literature. See for example, Cuatrecases, J. Biol. Chem. 245, 3059 (1970).

The length of the linking groups will vary widely depending upon the nature of the compound being linked, the effect of distance between the label and the particle on the label's properties, the potential for cross-linking of the labels, and the like.

In the subject invention, therefore, combinations of particles are employed where a first enzymatic reaction is involved to provide a substrate for a second enzymatic reaction, where the enzymes are conjugated to different particles. The second enzymatic reaction involves the production of a compound which can be determined spectrophotometrically due to absorption of light, particularly over 300 nm, preferably over 350 nm, and more preferably over 400 nm, fluorescence, where the light emitted is of a wavelength greater than 350 nm, preferably greater than 400 nm, and more preferably greater than 450 nm or through chemiluminescence. The extinction coefficient should be greater than $10^3 mol^{-1} cm^{-1}$, preferably greater than $10^4$ for absorption at the indicated wavelengths.

Particle Conjugate

The particle conjugates will always be conjugated or adsorbed to a mip where the mips may be the same or different in association with the different enzymes. The conjugation or adsorbtion may be direct or indirect. By direct conjugation is intended covalent bonding of the specific mip to the particle. Alternatively, one can employ receptor for the mip member. Where the mip is multivalent an impure preparation of a complementary member may be covalently bonded to the particle. Noncovlent binding of the unpurified mip then gives a particle labeled with the mip, so that all enzymes are conjugated through the intermediacy of the particle to at least one mip. In effect, all the enzyme bound to particles is capable of being involved in agglutination since there is also a mip bound to the particle.

A modification of the above situation may be employed where the analyte is a receptor such as human IgE. One could covalently bond an allergen recognized by the IgE to the particle. The other particle conjugate would have anti(human IgE). In the assay, the human IgE analyte would bind to the allergen on the particle and the anti(human IgE) particle conjugate would bind to the human IgE bound to the particle. This situation differs from the general situation since the binding of the analyte to the particles during the assay produces what has been defined as the particle conjugate. Also, other receptors such IgA, IgG, IgM, enzymes, specific receptors such as for estriol, biotin and other drugs, etc. may be similarly employed.

In effect, there are two specific binding pairs, where the same compound plays the role of ligand in one pair and receptor in the other, while the complementary members to the analyte of each of the mips need not have any relationship of ligand and receptor.

The ratio of the number of mips to the molecular weight of the particle will vary widely, depending upon the nature of the particle, the available surface area, the available binding sites, and the like. There will be on the average at least about one mip per particle and generally at least about one per $1 \times 10^8$ molecular weight, more usually at least about one per $1 \times 10^6$ molecular weight.

The ratio of the number of enzymes per particle molecular weight will vary widely. There will be on the average at least about one enzyme per particle and generally at least about one per $1 \times 10^8$ molecular weight, more usually at least about one per $1 \times 10^6$ molecular weight. The molecular ratio of mip to enzymes on the particle will be about 0.01 to 100:1, more usually 0.05 to 20:1. The ratio of enzymes per particle, as between the first enzyme and the second enzyme will be varied empirically to obtain the optimum results.

Ancillary Materials

Various ancillary materials may be employed in the subject assays. Particularly, enzyme substrates, cofactors, buffers, stabilizers, biocides, detergents, specialized additives and the like may be added to the assay medium. Those materials which are not involved in the production of the signal generally will be present in relatively small amounts, usually less than about 1M, more usually less than about 0.5M. Buffers will normally be present to provide assay medium concentrations of at least about 10 mM. Particular materials include non-ionic detergents, sodium azide, serum albumin, gamma globulin, tris, trace metals, salts, sodium chloride, etc.

Kits

As a matter of convenience, the reagent can be provided in kits, where the reagents are in predetermined ratios, so as to substantially optimize the sensitivity of the assay in the range of interest. After reconstitution of the reagents, the particle conjugates will normally be dispersed in an aqueous medium of substantially the same density as the particles, so the particles remain substantially uniformly dispersed or dispersible. By employing high density additives or adjusting the density of the particles, the desired density can be achieved.

Included with the kits will normally be the ancillary materials, substrates, and any other reagent necessary for performing the assay. As already indicated, depending upon the nature of the mips bound to the enzyme particle conjugates, the two enzyme particle conjugates may be in the same or different containers.

Experimental

The following examples are offered by way of illustration and not by way of limitation.

All percents in parts not otherwise indicated are by weight, except for mixtures of liquids which are by volume. All temperatures not otherwise indicated are Centigrade. The following abbreviations will have the following meaning: GO-glucose oxidase; PRP-polyribophosphate capsular antigen of *Haemophilus influenzae* type b; HRP-horseradish peroxidase; ABTS-2,2'-azino-di-(3-ethylbenzthiazoline-6-sulfonic acid). Readings were made on an Artek Vertical Beam spectrophotometer.

EXAMPLE 1

GO-anti(PRP) latex particles

Amine substituted latex (0.5µ nominal diameter, number 7763, Polysciences) was prepared for conjugation as follows. Approximately 2 ml of the particle suspension (25 mg/ml) was washed 3 times with 10 mM sodium carbonate, pH 9.6, by adding 35 ml of the buffer, spinning the suspension for 30 minutes at 16,500 rpm in the SA-600 head of a Sorvall RC5B centrifuge and then resuspending the packed particles in the original volume of the same buffer.

Aldehyde glucose oxidase and aldehyde antibody for coupling to the particles were prepared in the following manner. Native glucose oxidase (Sigma Cat. No. G-6500) or antibody to polyribophosphate (N.Y. State Department of Health lot 28A) at concentrations of approximately 4–10 mg/ml were dialyzed against distilled water ($3 \times 300$ ml for 3 hours each change). The pH of the retentate was between 4.5 and 5.0. To 2.5 ml of dialyzed antibody or glucose oxidase was added 0.5 ml 0.1M $NaIO_4$ in distilled water. The solution was stirred for 20 minutes at room temperature and then 30 µl 1.5M glycerol in distilled water was added. After stirring for an additional 30 minutes at room temperature the solution of aldehyde protein was dialyzed against 3x300ml 2mM sodium acetate pH4.5. The coupling of the aldehyde proteins to the latex particles was carried out in the following manner. One ml (25 mg) of the latex was combined with 0.31 ml (1.2 mg) of aldehyde activated GO, 0.24 ml (1.2 mg) of aldehyde activated antiPRP antibody and 0.85 ml of 10 mM sodium carbonate, pH 9.6 and the pH adjusted to 9.6 with 0.1N NaOH.

The GO and antibody were initially mixed and then added to the buffer-latex mixture. After incubating the mixture for two hours at room temperature, it was cooled to 0° and 0.1 volume of 4 mg/ml sodium borohydride in distilled water was added. The mixture was stirred at 0° for 1.5 hours and then diluted to 35 ml with PBS-Tween 20 (10 mM sodium phosphate, pH 7.2, 0.15M NaCl, 0.05% Tween 20). The suspension was spun down for 30 minutes at 16,500 rpm as described previously and the precipitate resuspended by vigorous vortexing in 1 ml PBS Tween and the suspension stored overnight. After washing three additional times with 35 ml PBS-Tween, the sample was suspended in PBS-Tween (10 ml) to provide a 2.5 mg/ml suspension or 1:10 dilution of the original latex suspension.

EXAMPLE 2

HRP and antiPRP latex particles

To prepare the HRP for use, 15 mg of HRP (lot 120F 9695 Sigma) was dissolved in 2 ml of distilled water to provide a concentration of 4.7 mg/ml based upon heme absorption. The HRP was activated by cleavage of sugar residues using the following procedure: To the above solution of HRP was added 0.4 ml 0.1M sodium periodate and the solution allowed to stand for 20 min at room temperature. At the end of the 20 min incubation, 0.24 ml 1M glycerol was added and the solution allowed to stand for an additional 30 minutes at room temperature. The product was dialyzed 3x against 300 ml 2 mM sodium acetate, pH 4.5.

Prior to coupling, the latex was treated in the same manner as described in Example 1. The coupling was carried out in the following manner: 1 ml (25 mg/ml) of the latex in the sodium carbonate buffer was mixed with 0.70 ml of the carbonate buffer, and a mixture of 0.38 ml (0.64 mg) of the aldehyde activated HRP in 2 mM sodium acetate, pH 4.5 and 0.32 ml (1.2 mg) of the aldehyde activated antiPRP antibody in the same acetate buffer, added to the latex suspension. To the mixture was then added 0.1 ml of 60 mM sodium carbonate, pH 9.6 and the pH was adjusted to 9.6 with 0.1N sodium hydroxide. The final volume was 2.5 ml.

The reaction mixture was incubated for two hours at room temperature, the suspension cooled to 0° and 0.1 volume of 4 mg/ml sodium borohydride in distilled water added. After stirring for 2 hr at 0°, 7.5 ml of PBS-Tween was added and the suspension spun down for 25 min as described in Example 1. The pellets were washed 3X with 35 ml PBS-Tween and the latex particles resuspended in 10 ml PBS-Tween to provide a 2.5 mg/ml suspension, a 1:10 dilution of the original stock solution.

In order to demonstrate the subject invention, the following assay was carried out for PRP.

A mixture was prepared of 8 µl of the GO-antiPRP latex beads and 2 µl of the HRP-antiPRP beads and placed in wells of Costar Serocluster EIA plates (CAT no. 3596), followed by the addition of 100 µl of a solution containing a predetermined concentration of PRP. The range of concentration used was from 0 to 100 ng/ml. After incubating for 60 min at 37° C. with shaking, to the mixture was then added 100 µl of developer containing 500 mM glucose, 20 mM ABTS, 1.6 mg/ml ovalbumin and 40 µg/ml catalase. The absorption at 450 nm was determined at 15 minutes and 30 minutes after the addition of the developer and the difference graphed against concentration. The following table indicates the results.

TABLE V

| PRP conc. ng/ml | Absorbance 405 nm 30 min–15 min |
| --- | --- |
| 0 | 0.10 |
| 0.05 | 0.095 |
| 0.1 | 0.12 |
| 0.5 | 0.33 |
| 1.0 | 0.50 |
| 5.0 | 0.61 |
| 10.0 | 0.56 |
| 50.0 | 0.63 |
| 100.0 | 0.63 |

The above results demonstrate that there is a substantial difference between the blank and 0.5 ng/ml PRP. The signal varies from 0.1 to 0.5 over the range of 0 to 1.0 ng/ml of PRP. Thus, the results provide a sensitive assay for the determination of PRP.

Use of the subject method provides many advantages which have previously been disclosed for other "homogeneous" assays, while providing greater sensitivity and ease of protocol. The reagents are easily prepared. The agglutination does not interfere with the absorption difference readings, so that one can use electromagnetic absorption or emission as the detectable signal.

Although the foregoing invention has been described in some detail by way of illustration and example for purposes of clarity of understanding, it will be obvious that certain changes and modifications may be practiced within the scope of the appended claims.

What is claimed is:

1. An assay method for determining the presence in a sample of an analyte, which analyte is a member of a specific binding pair ("mip") consisting of ligand and its homologous receptor;

said method employing:

(a) a continuous aqueous medium;

(b) first and second discrete dispersible solid particle conjugates to which are conjugated mips, a first enzyme conjugated to said first particle and a second enzyme conjugated to said second particle, where said first and second enzymes are related by the product of said first enzyme being the substrate of said second enzyme;

(c) a signal producing system capable of producing a detectable signal, said system comprising said first and second enzymes, substrate for said first enzyme, and any additional substrates for said second enzyme other than said product of said first enzyme, wherein the reaction of said second enzyme results in a second product producing a detectable signal; and wherein the amount of agglutination of said particles bringing said first and said second enzymes into close proximity is related to the amount of analyte in said sample;

said method comprising:

combining in an aqueous assay medium, (a) said sample;

(b) said particle conjugates substantially uniformly dispersed in said medium;

(c) said substrate for said first enzyme;

(d) the homologous member of said specific binding pair, when the particle conjugates have the same mip which corresponds to the analyte; and determining the level of the signal resulting from said second product in said assay medium as compared to an assay medium having a known amount of analyte.

2. A method according to claim 1, where said aqueous assay medium is at a temperature in the range of about 10°–50° C., at a pH in the range of about 5–10, and said signal producing system includes a scavenger which modifies said product of said first enzyme to a compound which is inactive with said second enzyme.

3. A method according to claim 2, where at least one of said enzymes is an oxidoreductase.

4. A method according to claim 3, wherein one of said enzymes is horse radish peroxidase.

5. A method according to any of claims 3 or 4, where said first enzyme is glucose oxidase.

6. A method according to claim 2, wherein said analyte is a hapten.

7. A method according to claim 2, wherein said analyte is an antigen.

8. A kit for use in an immunoassay for determining the presence in a sample of an analyte, which analyte is a member of a specific binding pair ("mip") consisting of ligand and its homologous receptor;

said method employing:

(a) a continuous aqueous medium;

(b) first and second discrete dispersible solid particle conjugates to which are conjugated mips, a first enzyme conjugated to said first particle and a second enzyme conjugated to said second particle, where said first and second enzymes are related by the product of said first enzyme being the substrate of said second enzyme;

(c) a signal producing system capable of producing a detectable signal, said system comprising said first and second enzymes, substrate for said first enzyme, and any additional substrates for said second enzyme other than said product of said first enzyme, wherein the reaction of said second enzyme results in a second product producing a detectable signal; and wherein the amount of agglutination of said particles bringing said first and said second enzymes into close proximity is related to the amount of analyte in said sample;

said method comprising:
combining in an aqueous assay medium,
(a) said sample;
(b) said particle conjugates substantially uniformly dispersed in said medium;
(c) said substrate for said first enzyme;
(d) the homologous member of said specific binding pair, when the particle conjugates have the same mip which corresponds to the analyte; and
determining the level of the signal resulting from said second product in said assay medium as compared to an assay medium having a known amount of analyte; said kit comprising, in packaged combination in relative amounts to substantially optimize the sensitivity of said assay, first and second discrete dispersible solid particle conjugates, each of said particle conjugates having mips conjugated thereto and a first enzyme conjugated to said first particle and a second enzyme conjugated to said second particle, where the two enzymes are related by the product of said first enzyme being the substrate of said second enzyme and wherein the reaction of said second enzyme results in a product providing a detectable signal.

9. A kit according to claim 8, including a scavenger which modifies said product of said first enzyme to a compound which is inactive with said second enzyme.

10. A kit according to claim 9, when said first enzyme is glucose oxidase and said second enzyme is horse radish peroxidase and said scavenger is catalase.

* * * * *